US011337667B2

(12) United States Patent
Wang et al.

(10) Patent No.: US 11,337,667 B2
(45) Date of Patent: *May 24, 2022

(54) SYSTEMS AND METHODS FOR DETERMINING ROTATION ANGLES

(71) Applicant: SHANGHAI UNITED IMAGING HEALTHCARE CO., LTD., Shanghai (CN)

(72) Inventors: Jingbo Wang, Shanghai (CN); Weiqiang Guo, Shanghai (CN); Xiangyu Hua, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 8 days.

This patent is subject to a terminal disclaimer.

(21) Appl. No.: 16/877,174

(22) Filed: May 18, 2020

(65) Prior Publication Data

US 2020/0278200 A1 Sep. 3, 2020

Related U.S. Application Data

(63) Continuation of application No. 15/798,432, filed on Oct. 31, 2017, now Pat. No. 10,655,958, which is a (Continued)

(51) Int. Cl.
*A61B 6/03* (2006.01)
*G06T 11/00* (2006.01)
(Continued)

(52) U.S. Cl.
CPC ............ *A61B 6/5258* (2013.01); *A61B 6/032* (2013.01); *A61B 6/5205* (2013.01); (Continued)

(58) Field of Classification Search
None
See application file for complete search history.

(56) References Cited

U.S. PATENT DOCUMENTS 6,169,778 B1 * 1/2001 Schmidt ................. A61B 6/032
378/15
6,466,640 B1 10/2002 Taguchi
(Continued)

FOREIGN PATENT DOCUMENTS

CN 101327127 A * 12/2008 ............ A61B 6/032
CN 103976753 A 8/2014
(Continued)

OTHER PUBLICATIONS

The Extended European Search Report in European Application No. 17923553.6 dated Sep. 21, 2020, 7 pages.
(Continued)

*Primary Examiner* — Thomas R Artman
(74) *Attorney, Agent, or Firm* — Metis IP LLC

(57) ABSTRACT

The present disclosure relates to systems and methods for determining rotation angles. The systems may perform the methods to: obtain a rotation speed of a radioactive scanning source in a CT scanner; obtain a plurality of original projection acquisition times corresponding to a plurality of projection samples, the plurality of projection samples being associated with rotation of the radioactive scanning source; determine a plurality of original rotation angles corresponding to the plurality of projection samples based on the plurality of original projection acquisition times and the rotation speed of the radioactive scanning source; and determine a plurality of modified rotation angles corresponding to the plurality of projection samples by modifying the plurality of original rotation angles.

20 Claims, 8 Drawing Sheets

Related U.S. Application Data continuation of application No. PCT/CN2017/099347, filed on Aug. 28, 2017.

(51) Int. Cl.
    *G01N 23/046*     (2018.01)
    *A61B 6/00*     (2006.01)
    *G01B 15/00*     (2006.01)

(52) U.S. Cl.
    CPC ............ *A61B 6/5294* (2013.01); *G01B 15/00* (2013.01); *G01N 23/046* (2013.01); *G06T 11/005* (2013.01); *A61B 6/035* (2013.01); *G01N 2223/304* (2013.01); *G01N 2223/306* (2013.01); *G01N 2223/401* (2013.01)

(56) References Cited

U.S. PATENT DOCUMENTS

| | | | |
|---|---|---|---|
| 7,263,157 B2 * | 8/2007 | Bruder | A61B 6/032 378/15 |
| 7,277,525 B2 | 10/2007 | Tsujii | |
| 9,408,579 B2 | 8/2016 | Yamakawa et al. | |
| 9,668,705 B2 | 6/2017 | Yamakawa et al. | |
| 9,724,051 B2 | 8/2017 | Yoshimura et al. | |
| 10,655,958 B2 * | 5/2020 | Wang | A61B 6/5294 |
| 2006/0018423 A1 * | 1/2006 | Bruder | A61B 6/4014 378/9 |
| 2014/0023175 A1 | 1/2014 | Yamaguchi | |
| 2015/0030118 A1 | 1/2015 | Nakanishi et al. | |
| 2016/0166228 A1 | 6/2016 | Li | |
| 2017/0291043 A1 | 10/2017 | Ju et al. | |
| 2019/0063912 A1 | 2/2019 | Wang et al. | |
| 2020/0278200 A1 * | 9/2020 | Wang | G01N 23/046 |

FOREIGN PATENT DOCUMENTS

| | | |
|---|---|---|
| CN | 104173072 A | 12/2014 |
| CN | 106821403 A | 6/2017 |
| JP | 2006138715 A | 6/2006 |
| JP | 2011152325 A | 8/2011 |
| WO | 2014166550 A1 | 10/2014 |

OTHER PUBLICATIONS

First Office Action in Chinese Application No. 201810693385.2 dated Apr. 28, 2021, 15 pages.
International Search Report in International Application No. PCT/CN2017/099347 dated May 22, 2018, 5 pages.
Written Opinion in International Application No. PCT/CN2017/099347 dated May 22, 2018, 4 pages.

* cited by examiner

SYSTEMS AND METHODS FOR DETERMINING ROTATION ANGLES

CROSS-REFERENCE TO RELATED APPLICATIONS

This application is a continuation of U.S. application Ser. No. 15/798,432, filed on Oct. 31, 2017, which is a continuation of International Application No. PCT/CN2017/099347 filed on Aug. 28, 2017, the entire contents of each of which are hereby incorporated by reference.

TECHNICAL FIELD

The present disclosure generally relates to image reconstruction of computed tomography (CT), and more specifically, relates to methods and systems to determine rotation angles of CT.

BACKGROUND

Computed tomography (CT) has been widely used in medical diagnosis. CT is a technology that makes use of computer-processed combinations of X-ray images taken from different angles of an object to produce cross-sectional images. Angle information (e.g., rotation angle) of CT may be important in CT image reconstruction. During a CT scan, a CT scanner may acquire a plurality of projection samples to keep track of rotation angles of a radioactive scanning source. The CT scanner may record a plurality of projection acquisition times for the plurality of projection samples. However, because of a system error of the CT scanner (e.g., an error of hardware of the CT scanner, an error of data transmission of the CT scanner, etc.), there may be an error in the recorded projection acquisition times, which may cause an error in the determination of rotation angles. The error in the rotation angles may cause artifacts (e.g., staircase artifacts) in a reconstructed CT image. Therefore, it is desirable to provide systems and methods for determining rotation angles to reduce/eliminate the error in the recorded projection acquisition times.

SUMMARY

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

According to a first aspect of the present disclosure, a system may include one or more storage media and one or more processors configured to communicate with the one or more storage media. The one or more storage media may include a set of instructions for analyzing data from a computer tomography (CT) scanner. When the one or more processors executing the set of instructions, the one or more processors may be directed to perform one or more of the following operations. The one or more processors may obtain a rotation speed of a radioactive scanning source in the CT scanner. The one or more processors may obtain a plurality of original projection acquisition times corresponding to a plurality of projection samples, the plurality of projection samples being associated with rotation of the radioactive scanning source. The one or more processors may determine a plurality of original rotation angles corresponding to the plurality of projection samples based on the plurality of original projection acquisition times and the rotation speed of the radioactive scanning source. The one or more processors may determine a plurality of modified rotation angles corresponding to the plurality of projection samples by modifying the plurality of original rotation angles.

In some embodiments, the one or more processors may determine one or more interpolation rotation angles based on the plurality of modified rotation angles.

In some embodiments, to determine the one or more interpolation rotation angles based on the plurality of modified rotation angles, the one or more processors may obtain one or more view acquisition times associated with one or more view samples, the one or more view samples being associated with X-rays of the CT scanner. The one or more processors may determine the one or more interpolation rotation angles based on the one or more view acquisition times and the plurality of modified rotation angles.

In some embodiments, to determine the plurality of modified rotation angles corresponding to the plurality of projection samples by modifying the plurality of original rotation angles, the one or more processors may obtain a plurality of standard rotation angles corresponding to the plurality of projection samples. The one or more processors may compare the plurality of original rotation angles with the plurality of corresponding standard rotation angles, respectively. The one or more processors may modify the plurality of original rotation angles based on the plurality of standard rotation angles and the comparison.

In some embodiments, to obtain the plurality of standard rotation angles corresponding to the plurality of projection samples, the one or more processors may obtain a sample number of the plurality of projection samples. The one or more processors may determine, based on the sample number of the plurality of projection samples, a standard angle difference corresponding to any two neighboring projection samples arranged in time order. The one or more processors may determine the plurality of standard rotation angles based on the standard angle difference.

In some embodiments, to obtain the plurality of standard rotation angles corresponding to the plurality of projection samples, the one or more processors may obtain a sample number of the plurality of projection samples. The one or more processors may determine, based on the sample number of the plurality of projection samples and the rotation speed of the radioactive scanning source, a standard time difference corresponding to any two neighboring projection samples arranged in time order. The one or more processors may determine a standard angle difference corresponding to any two neighboring projection samples arranged in time order based on the rotation speed of the radioactive scanning source and the standard time difference. The one or more processors may determine the plurality of standard rotation angles based on the standard angle difference.

In some embodiments, to determine the plurality of modified rotation angles corresponding to the plurality of projection samples by modifying the plurality of original rotation angles, the one or more processors may obtain a standard angle difference value corresponding to any two neighboring projection samples of the plurality of projection samples arranged in time order. The one or more processors may determine a plurality of original difference values each of which corresponds to two neighbor original rotation angles of the plurality of original rotation angles arranging in order of time. The one or more processors may compare the plurality of the original difference values with the standard difference value, respectively. The one or more processors may modify the plurality of original difference values based on the standard difference value and the comparison. The one or more processors may determine the plurality of modified rotation angles based on the plurality of modified difference values.

According to another aspect of the present disclosure, a system may include one or more storage media and one or more processors configured to communicate with the one or more storage media. The one or more storage media may include a set of instructions for analyzing data from a computer tomography (CT) scanner. When the one or more processors executing the set of instructions, the one or more processors may be directed to perform one or more of the following operations. The one or more processors may obtain a rotation speed of a radioactive scanning source in the CT scanner. The one or more processors may obtain a plurality of original projection acquisition times corresponding to the plurality of projection samples, the plurality of projection samples being associated with rotation of the radioactive scanning source. The one or more processors may determine a plurality of modified projection acquisition times corresponding to the plurality of projection samples by modifying the plurality of original projection acquisition times. The one or more processors may determine a plurality of modified rotation angles corresponding to the plurality of projection samples based on the rotation speed of the radioactive scanning source and the plurality of modified projection acquisition times.

In some embodiments, the one or more processors may determine one or more interpolation rotation angles based on the plurality of modified rotation angles.

In some embodiments, to determine the one or more interpolation rotation angles based on the plurality of modified rotation angles, the one or more may obtain one or more view acquisition times associated with one or more view samples, the one or more view samples being associated with X-rays of the CT scanner. The one or more processors may determine the one or more interpolation rotation angles based on the one or more view acquisition times and the plurality of modified rotation angles.

In some embodiments, to determine the plurality of modified projection acquisition times, the one or more processors may obtain a plurality of standard projection acquisition times corresponding to the plurality of projection samples. The one or more processors may compare the plurality of original projection acquisition times with the plurality of corresponding standard projection acquisition times, respectively. The one or more processors may modify the plurality of original projection acquisition times based on the plurality of standard projection acquisition times and the comparison.

In some embodiments, to obtain the plurality of standard projection acquisition times corresponding to the plurality of projection samples, the one or more processors may obtain a sample number of the plurality of projection samples. The one or more processors may determine a standard time difference value corresponding to any two neighboring projection samples of the plurality of projection samples arranged in time order based on the sample number of the plurality of projection samples and the rotation speed of the radioactive scanning source. The one or more processors may determine the plurality of standard projection acquisition times based on the standard time difference value.

In some embodiments, to determine the plurality of modified projection acquisition times, the one or more processors may obtain a standard time difference value corresponding to any two neighboring projection samples of the plurality of projection samples arranged in time order. The one or more processors may determine a plurality of original time difference values each of which corresponds to two neighbor original projection acquisition times of the plurality of original projection acquisition times. The one or more processors may compare the plurality of original time difference values with the standard time difference value, respectively. The one or more processors may modify the plurality of original time difference values based on the standard time difference value and the comparison. The one or more processors may determine the plurality of modified projection acquisition times based on the plurality of modified time difference values.

According to yet another aspect of the present disclosure, a method may include one or more of the following operations. One or more processors may obtain a rotation speed of a radioactive scanning source in a CT scanner. The one or more processors may obtain a plurality of original projection acquisition times corresponding to a plurality of projection samples, the plurality of projection samples being associated with rotation of the radioactive scanning source. The one or more processors may determine a plurality of original rotation angles corresponding to the plurality of projection samples based on the plurality of original projection acquisition times and the rotation speed of the radioactive scanning source. The one or more processors may determine a plurality of modified rotation angles corresponding to the plurality of projection samples by modifying the plurality of original rotation angles.

According to yet another aspect of the present disclosure, a method may include one or more of the following operations. One or more processors may obtain a rotation speed of a radioactive scanning source in a CT scanner. The one or more processors may obtain a plurality of original projection acquisition times corresponding to the plurality of projection samples, the plurality of projection samples being associated with rotation of the radioactive scanning source. The one or more processors may determine a plurality of modified projection acquisition times corresponding to the plurality of projection samples by modifying the plurality of original projection acquisition times. The one or more processors may determine a plurality of modified rotation angles corresponding to the plurality of projection samples based on the rotation speed of the radioactive scanning source and the plurality of modified projection acquisition times.

According to yet another aspect of the present disclosure, a system may comprise: a system information obtaining module configured to obtain a rotation speed of a radioactive scanning source in a CT scanner; a time obtaining module configured to obtain a plurality of original projection acquisition times corresponding to a plurality of projection samples, the plurality of projection samples being associated with rotation of the radioactive scanning source; and a modification module configured to determine a plurality of original rotation angles corresponding to the plurality of projection samples based on the plurality of original projection acquisition times and the rotation speed of the radioactive scanning source, and determine a plurality of modified rotation angles corresponding to the plurality of projection samples by modifying the plurality of original rotation angles.

According to yet another aspect of the present disclosure, a system may comprise: a system information obtaining module configured to obtain a rotation speed of a radioactive scanning source in a CT scanner; a time obtaining module configured to obtain a plurality of original projection acquisition times corresponding to the plurality of projection samples, the plurality of projection samples being associated with rotation of the radioactive scanning source; and a modification module configured to determine a plurality of modified projection acquisition times corresponding to the plurality of projection samples by modifying the plurality of original projection acquisition times, and determine a plurality of modified rotation angles corresponding to the plurality of projection samples based on the rotation speed of the radioactive scanning source and the plurality of modified projection acquisition times.

According to yet another aspect of the present disclosure, a non-transitory computer readable medium may comprise at least one set of instructions. The at least one set of instructions may be executed by one or more processors of a computer server. The one or more processors may obtain a rotation speed of a radioactive scanning source in a CT scanner. The one or more processors may obtain a plurality of original projection acquisition times corresponding to a plurality of projection samples, the plurality of projection samples being associated with rotation of the radioactive scanning source. The one or more processors may determine a plurality of original rotation angles corresponding to the plurality of projection samples based on the plurality of original projection acquisition times and the rotation speed of the radioactive scanning source. The one or more processors may determine a plurality of modified rotation angles corresponding to the plurality of projection samples by modifying the plurality of original rotation angles.

According to yet another aspect of the present disclosure, a non-transitory computer readable medium may comprise at least one set of instructions. The at least one set of instructions may be executed by one or more processors of a computer server. The one or more processors may obtain a rotation speed of a radioactive scanning source in a CT scanner. The one or more processors may obtain a plurality of original projection acquisition times corresponding to the plurality of projection samples, the plurality of projection samples being associated with rotation of the radioactive scanning source. The one or more processors may determine a plurality of modified projection acquisition times corresponding to the plurality of projection samples by modifying the plurality of original projection acquisition times. The one or more processors may determine a plurality of modified rotation angles corresponding to the plurality of projection samples based on the rotation speed of the radioactive scanning source and the plurality of modified projection acquisition times.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
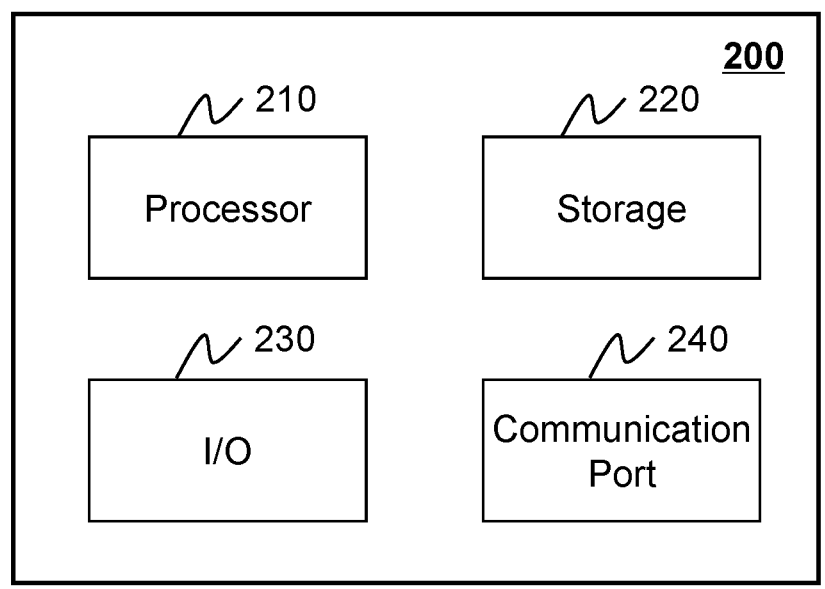
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., the processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be a computed tomography (CT) system, an emission computed tomography (ECT) system, a magnetic resonance imaging (MRI) system, an ultrasonography system, an X-ray photography system, a positron emission tomography (PET) system, or the like, or any combination thereof.

For illustration purposes, the disclosure describes systems and methods to determine rotation angles of CT for image reconstruction. During a CT scan, a CT scanner may acquire a plurality of projection samples to keep track of rotation angles of a radioactive scanning source. The CT scanner may record a plurality of projection acquisition times for the plurality of projection samples. The present disclosure provides systems and methods that perform modification to reduce/eliminate the error in the recorded projection acquisition times. Systems and methods in this disclosure may determine rotation angles based on the modification and determine one or more new rotation angles using a linear interpolation algorithm based on the rotation angles.

The following description is provided to help better understanding the processing methods and/or systems. This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
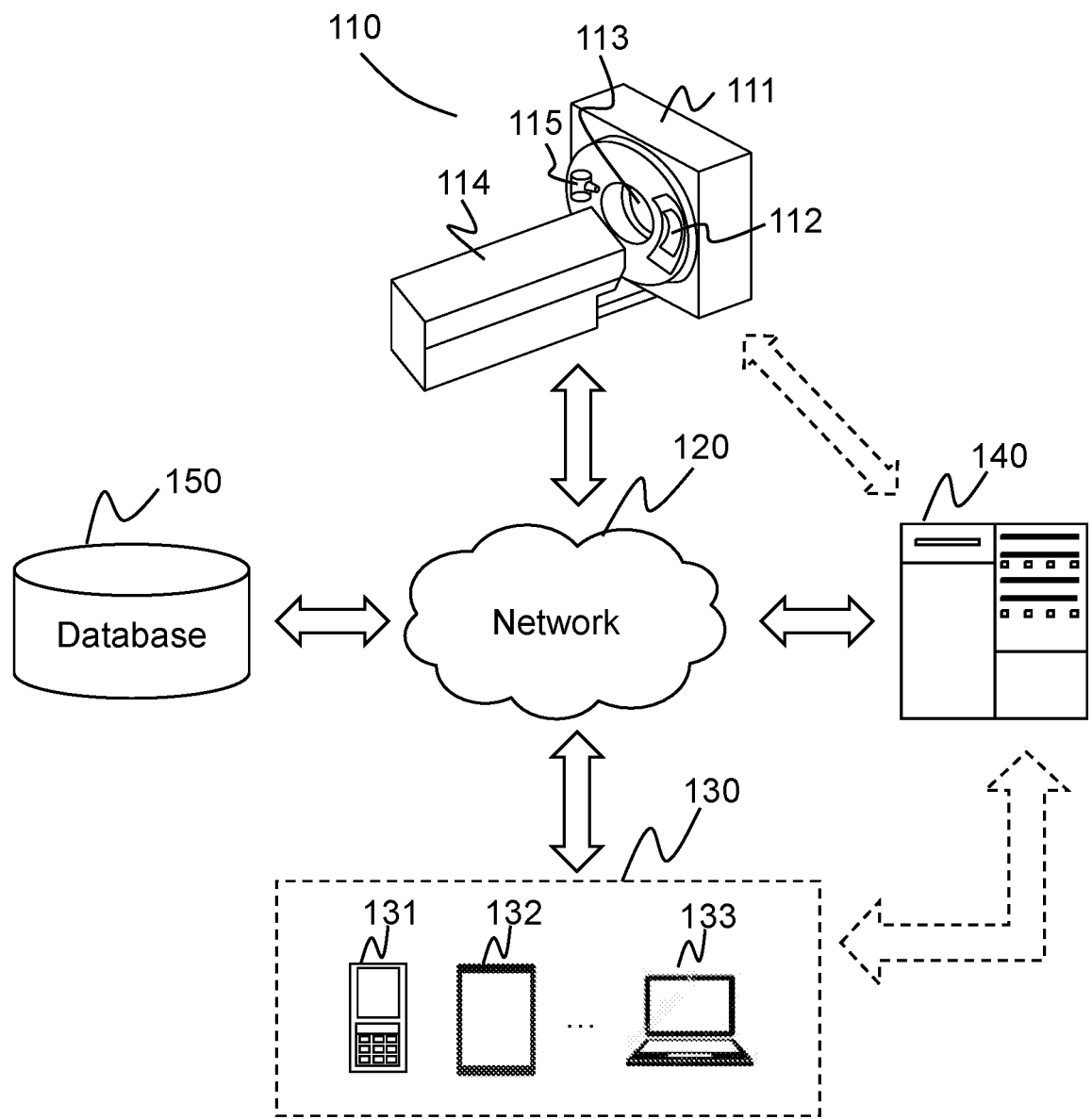
FIG. 1 is a schematic diagram illustrating an exemplary CT system according to some embodiments of the present disclosure.

FIG. 1 is a schematic diagrams illustrating an exemplary computed tomography (CT) system 100 according to some embodiments of the present disclosure. As shown in FIG. 1, the CT system 100 may include a CT scanner 110, a network 120, one or more terminals 130, a processing engine 140, and a database 150.

The CT scanner 110 may include a gantry 111, a detector 112, a detecting region 113, a table 114, and a radioactive scanning source 115. The gantry 111 may support the detector 112 and the radioactive scanning source 115. A scanned object may be placed on the table 114 for scanning. The radioactive scanning source 115 may emit radioactive rays to the scanned object. The detector 112 may detect radiation events (e.g., gamma photons) emitted from the detecting region 113. In some embodiments, the detector 112 may include one or more detector units. The detector units may include a scintillation detector (e.g., a cesium iodide detector), a gas detector, etc. The detector unit may be and/or include a single-row detector and/or a multi-rows detector.

The network 120 may include any suitable network that can facilitate exchange of information and/or data for the CT system 100. In some embodiments, one or more components of the CT system 100 (e.g., the CT scanner 110, the terminal 130, the processing engine 140, the database 150, etc.) may communicate information and/or data with one or more other components of the CT system 100 via the network 120. For example, the processing engine 140 may obtain information associated with the radioactive scanning source 115 from the CT scanner 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the CT system 100 may be connected to the network 120 to exchange data and/or information.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may process data and/or information obtained from the CT scanner 110, the terminal 130, and/or the database 150. For example, the processing engine 140 may obtain information associated with the radioactive scanning source 115 and modify the information associated with the radioactive scanning source 115. In some embodiments, the processing engine 140 may be a single server or a server group. The server group may be centralized or distributed. In some embodiments, the processing engine 140 may be local or remote. For example, the processing engine 140 may access information and/or data stored in the CT scanner 110, the terminal 130, and/or the database 150 via the network 120. As another example, the processing engine 140 may be directly connected to the CT scanner 110, the terminal 130 and/or the database 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2.

The database 150 may store data, instructions, and/or any other information. In some embodiments, the database 150 may store data obtained from the terminal 130 and/or the processing engine 140. In some embodiments, the database 150 may store data and/or instructions that the processing engine 140 and/or the terminal 130 may execute or use to perform exemplary methods described in the present disclosure. In some embodiments, the database 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the database 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the database 150 may be connected to the network 120 to communicate with one or more other components in the CT system 100 (e.g., the processing engine 140, the terminal 130, etc.). One or more components in the CT system 100 may access the data or instructions stored in the database 150 via the network 120. In some embodiments, the database 150 may be directly connected to or communicate with one or more other components in the CT system 100 (e.g., the CT scanner 110, the processing engine 140, the terminal 130, etc.). In some embodiments, the database 150 may be part of the processing engine 140.

FIG. 2 is a schematic diagram illustrating exemplary hardware and/or software components of an exemplary computing device 200 on which the processing engine 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may process information associated with the radioactive scanning source 115 obtained from the CT scanner 110, the terminal 130, the database 150, and/or any other component of the CT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the CT scanner 110, the terminal 130, the database 150, and/or any other component of the CT system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 140 for determining modified information associated with the radioactive scanning source 115 and determining new rotation angles associated with the radioactive scanning source 115.

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing engine 140 and the CT scanner 110, the terminal 130, and/or the database 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
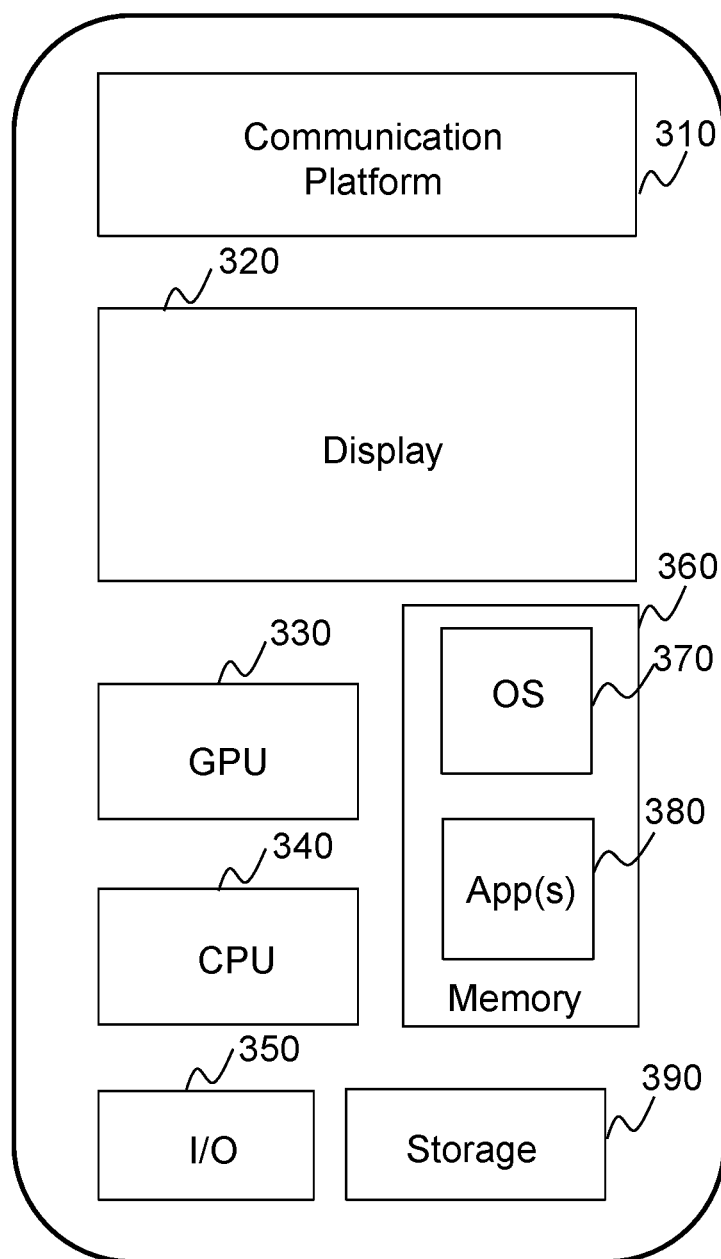
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 140. User interactions with the information stream may be achieved via the I/O 350 and provided to the processing engine 140 and/or other components of the CT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
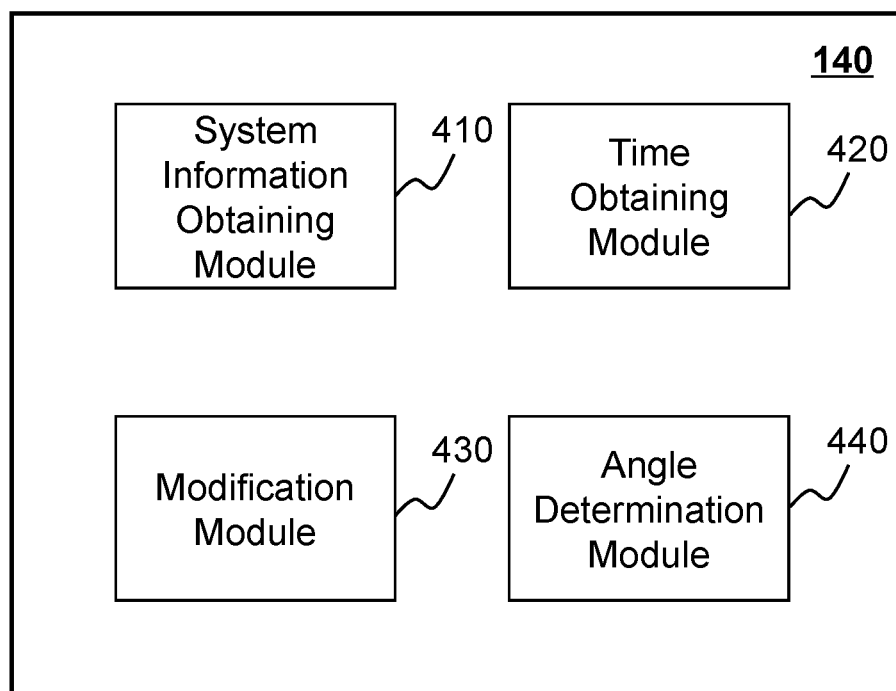
FIG. 4 is a block diagram illustrating an exemplary processing engine according to some embodiments of the present disclosure.

FIG. 4 is a block diagram illustrating an exemplary processing engine 140 according to some embodiments of the present disclosure. The processing engine 140 may include a system information obtaining module 410, a time obtaining module 420, a modification module 430, and an angle determination module 440.

The system information obtaining module 410 may obtain system information. In some embodiments, the system information may refer to information associated with one or more components of the CT scanner 110 such as the gantry 111, the detector 112, the table 114, and the radioactive scanning source 115, etc. In a CT scan, the radioactive scanning source 115 may emit X-rays to a scanned object located in the table 114. The X-rays may pass through the scanned object and may attenuate during the passing process. After passing through the scanned object, the attenuated X-rays may be detected by the detector 112. During the CT scan, the radioactive scanning source 115 may rotate around the scanned object with the gantry 111 at a constant or approximately constant speed. Because the radioactive scanning source 115 is fixed on the gantry 111, the rotation speed of the gantry 111 may be equal to or approximately equal to the rotation speed of the radioactive scanning source 115. During the CT scan, the CT scanner 110 may acquire a plurality of projection samples to keep track of rotation angles of the radioactive scanning source 115. Based on the CT scan, the system information obtaining module 410 may obtain the system information including a rotation speed of the gantry 111/the radioactive scanning source 115 and/or a sample number of projection samples acquired in a time period (e.g., a period for the radioactive scanning source 115 to go around for one rotation). Before the CT scan, a user of the CT system 100 (e.g., a doctor or a CT operator) may set the system information. For example, the user may set the rotation speed of the radioactive scanning source 115 as 2 rotations per second ($4\pi/s$), and set the sample number of projection samples acquired in a period for the radioactive scanning source 115 to go around for one rotation as 50. The user may set the system information through the processing engine 140 (e.g., the I/O 230) and/or the terminal 130 (e.g., the I/O 350). The system information set by the user may be stored in the database 150 and/or a storage device (e.g., the storage 220 of the processing engine 140, the storage 390 of the terminal 130, the memory 360 of the terminal 130, etc.). The system information obtaining module 410 may access the database 150 and/or the storage device to obtain the system information.

The time obtaining module 420 may obtain a plurality of original projection acquisition times corresponding to a plurality of projection samples. In some embodiments, the CT scanner 110 may record an original projection acquisition time for a projection sample. For example, the CT scanner 110 may add a time stamp to the projection sample. The CT scanner 110 may store the plurality of projection acquisition times in the database 150 and/or the storage device (e.g., the storage 220 of the processing engine 140, the storage 390 of the terminal 130, the memory 360 of the terminal 130, etc.). The time obtaining module 420 may access the database 150 and/or the storage device to obtain the plurality of original projection acquisition times.

The modification module 430 may perform modification associated with the plurality of projection samples based on the system information and the plurality of original projection acquisition times. The original projection acquisition time may be used to determine a rotation angle of the radioactive scanning source 115 corresponding to the projection sample. The rotation angle of the radioactive scanning source 115 may refer to an angle between a location of the radioactive scanning source 115 at a start time of the CT scan and a location of the radioactive scanning source 115 at a projection acquisition time. Rotation angles of the radioactive scanning source 115 may be important for CT image reconstruction. However, because of a system error of the CT scanner 110 (e.g., an error of hardware of the CT scanner 110, an error of data transmission of the CT scanner 110, etc.), there may be an error in the original projection acquisition time recorded by the CT scanner 110, which may cause an error in the determination of the rotation angle. The modification module 430 may perform modification associated with the projection samples to reduce/eliminate the error in the original projection acquisition times.

The angle determination module 440 may determine one or more new rotation angles (e.g., also referred to as interpolation rotation angles) based on the modification. In some embodiments, in the CT scan, the detector 112 may perform a plurality of view samples to keep track of the attenuation of X-rays. In the CT scan, the sample number of projection samples may be less than the sample number of view samples, and the number of rotation angles corresponding to the projection samples may be fewer than the sample number of view samples. The angle determination module 440 may determine one or more new rotation angles to make the total number of the rotation angles corresponding to the projection samples, and the new rotation angles equal to the sample number of the view samples. For example, in a period for the radioactive scanning source 115 to go around for one rotation, the detector 112 may acquire 2400 view samples, and the CT scanner 110 may acquire 300 projection samples. The angle determination module 440 may determine 2100 new rotation angles to match the sample number of view samples.

In some embodiments, one or more modules illustrated in FIG. 4 may be implemented in at least part of the exemplary CT system as illustrated in FIG. 1. For example, the system information obtaining 410, the time obtaining 420, the modification module 430, and/or the angle determination module 440 may be integrated into a console (not shown). Via the console, a user may set parameters for scanning an object, controlling processes of determining rotation angles, controlling parameters for reconstruction of an image, viewing reconstructed images, etc. In some embodiments, the console may be implemented via the processing engine 140 and/or the terminal 130.

The modules in the processing engine 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the system information obtaining module 410 may be integrated in the time obtaining module 420 as a single module which may both obtain the system information and the projection acquisition time.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing engine 140 may further include a storage module (not shown in FIG. 4). The storage module may be configured to store data generated during any process performed by any component of in the processing engine 140. As another example, each of components of the processing engine 140 may include a storage device. Additionally or alternatively, the components of the processing engine 140 may share a common storage device.

Figure 5:
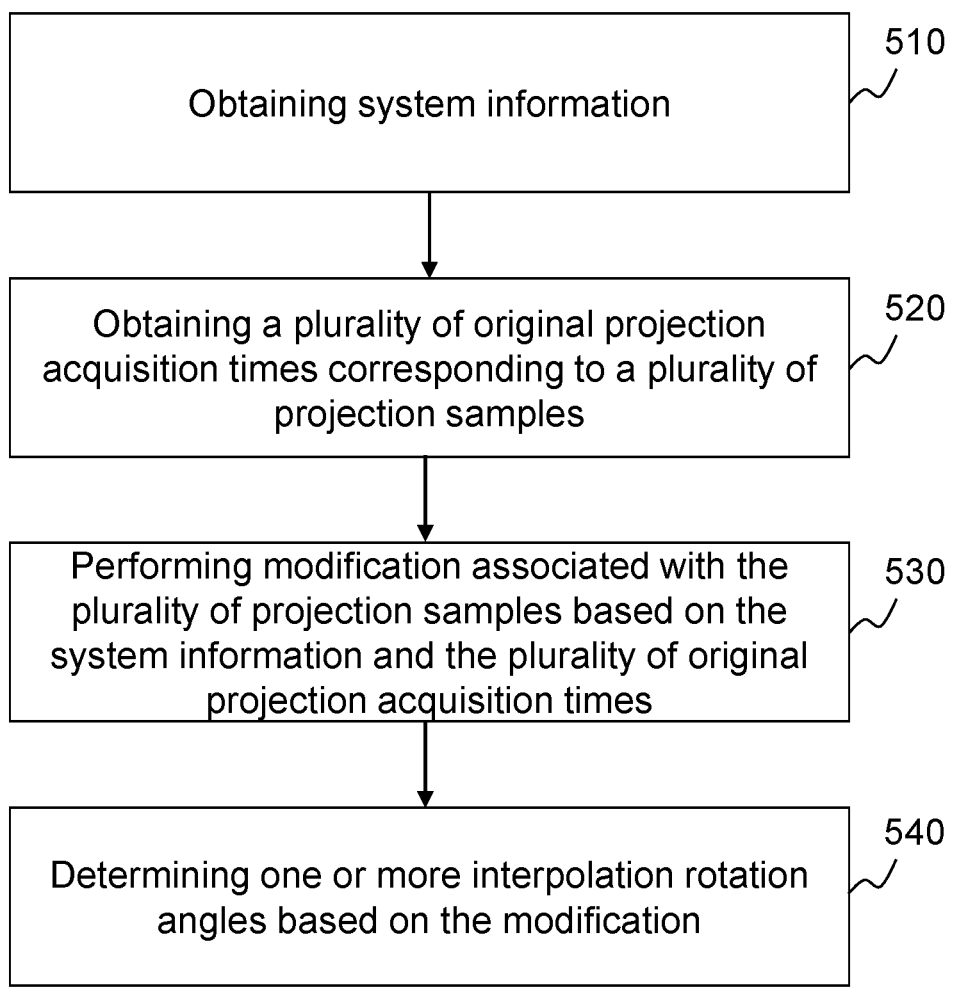
FIG. 5 is a flowchart illustrating an exemplary process for determining one or more new rotation angles according to some embodiments of the present disclosure.

FIG. 5 is a flowchart illustrating an exemplary process/method 500 for determining one or more new rotation angles according to some embodiments of the present disclosure. In some embodiments, the process/method 500 may be implemented in the system 100 illustrated in FIG. 1. For example, the process/method 500 may be stored in the database 150 and/or the storage device (e.g., the storage 220, the storage 390, the memory 360, etc.) as a form of instructions, and invoked and/or executed by the processing engine 140 (e.g., the processor 210 of the processing engine 140, or one or more modules in the processing engine 140 illustrated in FIG. 4) and/or the terminal 130 (e.g., the GUP 330 of the terminal 130, or the CUP 340 of the terminal 130). The operations of the illustrated process/method presented below are intended to be illustrative. In some embodiments, the process/method 500 may be accomplished with one or more additional operations not described, and/or without one or more of the operations discussed. Additionally, the order in which the operations of the process/method 500 as illustrated in FIG. 5 and described below is not intended to be limiting.

In 510, the system information obtaining module 410 may obtain system information. The system information may include a rotation speed of the radioactive scanning source 115 and/or the sample number of projection samples in a time period (e.g., a period for the radioactive scanning source 115 to go around for one rotation).

In 520, the time obtaining module 420 may obtain a plurality of original projection acquisition times corresponding to a plurality of projection samples. In some embodiments, the CT scanner 110 may record an original projection acquisition time for a projection sample. For example, the CT scanner 110 may add a time stamp to the projection sample. The CT scanner 110 may store the plurality of original projection acquisition times in the database 150 and/or the storage device (e.g., the storage 220 of the processing engine 140, the storage 390 of the terminal 130, the memory 360 of the terminal 130, etc.). The system information obtaining module 410 may access the database 150 and/or the storage device (e.g., the storage 220 of the processing engine 140, the storage 390 of the terminal 130, the memory 360 of the terminal 130, etc.) to obtain the plurality of original projection acquisition times.

In 530, the modification module 430 may perform modification associated with the plurality of projection samples based on the system information and the plurality of original projection acquisition times. The modification of the plurality of projection samples is to eliminate the effect caused by the error in the original projection acquisition times. In some embodiments, the modification module 430 may perform modification on the original projection acquisition times. In some embodiments, the modification module 430 may determine original intervals between each two neighboring projection samples based on the original projection acquisition times and perform modification on the original intervals. In some embodiments, the modification module 430 may determine original rotation angles corresponding to the projection samples based on the original projection acquisition times and perform modification on the original rotation angles. In some embodiments, the modification module 430 may determine original angle differences between each two original rotation angles corresponding to two neighboring projection samples and perform modification on the angle differences. The process of performing modification will be descried in detail in connection with FIG. 6 and/or FIG. 7.

In 540, the angle determination module 440 may determine one or more new rotation angles based on the modification. In some embodiments, the angle determination module 440 may determine one or more modified rotation angles based on the modification and determine the one or more new rotation angles based on the modified rotation angles. In some embodiments, a modified rotation angle may refer to a modified value of an original rotation angle. A new rotation angle may refer to a rotation angle generated based on one or more modified rotation angles. In some embodiments, the method of determining the one or more new rotation angles may include interpolation, extrapolation, smoothing, regression analysis, the least square method, or the like, or any combination thereof. Exemplary interpolation methods may include Lagrange interpolation, Newton interpolation, Hermite interpolation, piecewise interpolation, spline interpolation, linear interpolation, or the like, or a combination thereof. Exemplary extrapolation methods may include linear extrapolation, polynomial extrapolation, conic extrapolation, French curve extrapolation, or the like, or a combination thereof. Exemplary regression analysis may include linear regression, nonlinear regression, multiple regression, logistic regression, partial regression, or the like, or a combination thereof. As an example, the angle determination module 440 may use a linear interpolation algorithm to determine the one or more new rotation angles (e.g., as will be descried in detail in connection with FIG. 8).

In some embodiments, the processing engine 140 may perform step 510 and step 520 in any order. The processing engine 140 may perform step 510 before or after step 520. In some embodiments, the processing engine 140 may perform step 510 and step 520 simultaneously.

Figure 6:
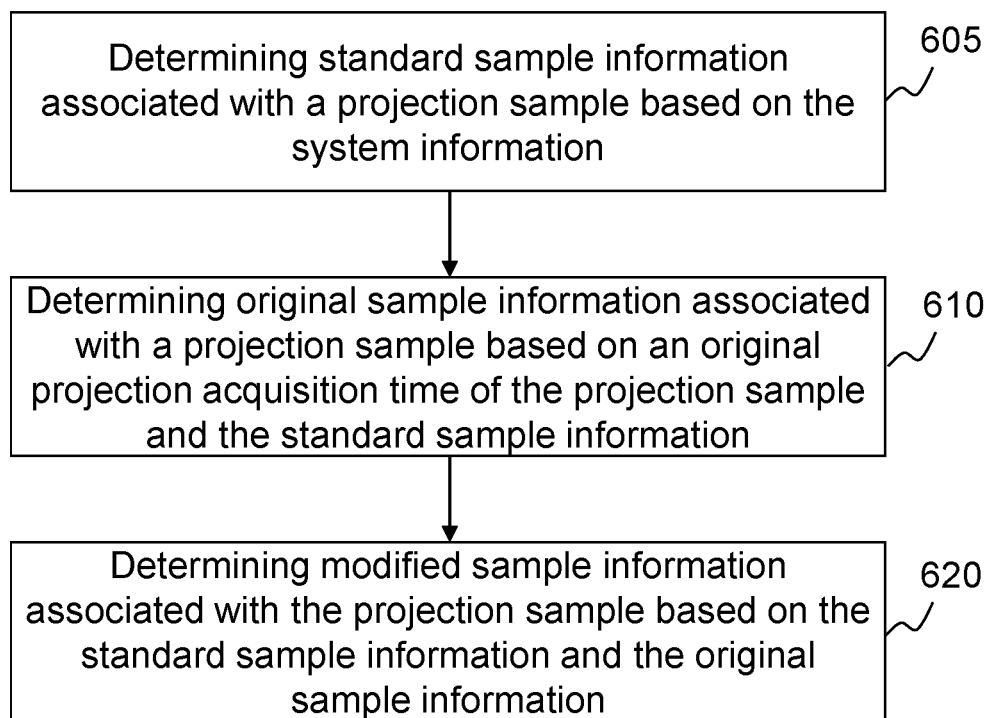
FIG. 6 is a flowchart illustrating an exemplary process for performing modification associated with a plurality of projection samples according to some embodiments of the present disclosure.

FIG. 6 is a flowchart illustrating an exemplary process/method 600 for performing modification associated with a plurality of projection samples according to some embodiments of the present disclosure. In some embodiments, the process/method 600 may be implemented in the system 100 illustrated in FIG. 1. For example, the process/method 600 may be stored in the database 150 and/or the storage device (e.g., the storage 220, the storage 390, the memory 360, etc.) as a form of instructions, and invoked and/or executed by the processing engine 140 (e.g., the processor 210 of the processing engine 140, or one or more modules in the processing engine 140 illustrated in FIG. 4) and/or the terminal 130 (e.g., the GUP 330 of the terminal 130, or the CUP 340 of the terminal 130). The operations of the illustrated process/method presented below are intended to be illustrative. In some embodiments, the process/method 600 may be accomplished with one or more additional operations not described, and/or without one or more of the operations discussed. Additionally, the order in which the operations of the process/method 600 as illustrated in FIG. 6 and described below is not intended to be limiting. In some embodiments, step 530 illustrated in FIG. 5 may be performed according to the process/method 600. In some embodiments, the process/method 600 may be used to determine modified sample information associated with one projection sample. In some embodiments, the modification module 430 may determine modified sample information associated with a plurality of projection samples based on the process/method 600 one by one or simultaneously.

In 605, the modification module 430 may determine standard sample information associated with a projection sample based on the system information. The standard sample information may include a standard projection acquisition time of the projection sample, a standard rotation angle of the projection sample, a standard interval between each two neighboring projection samples, a standard angle difference between each two neighboring projection samples, or the like, or any combination thereof.

In some embodiments, the modification module 430 may determine the standard interval based on the rotation speed of the radioactive scanning source 115 and the sample number of projection samples in a time period (e.g., a period for the radioactive scanning source 115 to go around for one rotation). For example, the user may set the rotation speed of the radioactive scanning source 115 as 2 rotations per second ($4\pi/s$), and set the sample number of projection samples in a period for the radioactive scanning source 115 to go around for one rotation as 50. The modification module 430 may determine the standard interval as 10 milliseconds.

In some embodiments, the modification module 430 may determine the standard projection acquisition time based on the standard interval. For example, the user may set the rotation speed of the radioactive scanning source 115 as 2 rotations per second ($4\pi/s$), and set the sample number of projection samples in a period for the radioactive scanning source 115 to go around for one rotation as 50. The standard interval may be 10 milliseconds based on the rotation speed of the radioactive scanning source 115 and the sample number of projection samples in a period for the radioactive scanning source 115 to go around for one rotation. The modification module 430 may determine the standard projection acquisition time by multiplying the standard interval by a sequence number of the projection sample. The sequence number of the projection sample may refer to an order in which the projection sample is acquired by the CT scanner 110 in the CT scan. For example, the sequence number of 3 may indicate that the projection sample is the third projection sample acquired by the CT scanner 110 in the CT scan, and the modification module 430 may determine the standard projection acquisition time of the projection sample as 10×3=30 milliseconds.

In some embodiments, the modification module 430 may determine the standard angle difference based on the rotation speed of the radioactive scanning source 115 and the sample number of projection samples in a time period (e.g., a period for the radioactive scanning source 115 to go around for one rotation). For example, the user may set the rotation speed of the radioactive scanning source 115 as 2 rotations per second (4π/s), and set the sample number of projection samples in a period for the radioactive scanning source 115 to go around for one rotation as 50. The modification module 430 may determine the standard interval as 0.04 π(≈0.1256).

In some embodiments, the modification module 430 may determine the standard rotation angle based on the standard angle difference. For example, the user may set the rotation speed of the radioactive scanning source 115 as 2 rotations per second (4π/s), and set the sample number of projection samples in a period for the radioactive scanning source 115 to go around for one rotation as 50. The standard angle difference may be 0.04 π based on the rotation speed of the radioactive scanning source 115 and the sample number of projection samples in a period for the radioactive scanning source 115 to go around for one rotation. The modification module 430 may determine the standard rotation angle by multiplying the standard angle difference by the sequence number of the projection sample. For example, the sequence number of the projection sample may be 3. The modification module 430 may determine the standard rotation angle of the projection sample as 0.04π×3=0.12 π.

In some embodiments, the modification module 430 may determine the standard rotation angle based on the standard projection acquisition time. Further, modification module 430 may determine the standard rotation angle by multiplying the standard projection acquisition time by the rotation speed of the radioactive scanning source 115. For example, the user may set the rotation speed of the radioactive scanning source 115 as 2 rotations per second (4π/s), and set the sample number of projection samples in a period for the radioactive scanning source 115 to go around for one rotation as 50. The sequence number of the projection sample may be 3. The modification module 430 may determine the standard projection acquisition time of the projection sample as 30 milliseconds. The modification module 430 may determine the standard rotation angle of the projection sample as 4π×0.03=0.12 π.

In 610, the modification module 430 may determine original sample information associated with a projection sample based on an original projection acquisition time of the projection sample and the system information. In some embodiments, the original sample information may include an original rotation angle of the projection sample, the original projection acquisition time of the projection sample, an original interval between a neighboring projection sample of the projection sample (e.g., a neighboring projection sample prior to the projection sample or behind the projection sample), an original angle difference between a neighboring projection sample of the projection sample (e.g., a neighboring projection sample prior to the projection sample or behind the projection sample).

In some embodiments, the modification module 430 may determine the original rotation angle based on the original projection acquisition time. Further, the modification module 430 may determine the original rotation angle by multiplying the original projection acquisition time by the rotation speed of the radioactive scanning source 115. For example, the user may set the rotation speed of the radioactive scanning source 115 as 2 rotations per second (4π/s). The original projection acquisition time of the projection sample may be 10 milliseconds. The modification module 430 may determine the original rotation angle of the projection sample as 0.04π.

In some embodiments, the modification module 430 may determine the original angle difference based on the original interval or the original rotation angle. For example, the modification module 430 may determine the original angle difference by multiplying the original interval by the rotation speed of radioactive scanning source 115. As another example, the modification module 430 may determine the original angle difference by determining a difference between the original rotation angle and an original rotation angle of a neighboring projection sample (e.g., a neighboring projection sample prior to the projection sample or behind the projection sample).

In 620, the modification module 430 may determine modified sample information associated with the projection sample based on the standard sample information and the original sample information. The modified sample information may include a modified projection acquisition time, a modified rotation angle, a modified interval between a neighboring projection sample of the projection sample (e.g., a neighboring projection sample prior to the projection sample or behind the projection sample), a modified angle difference between a neighboring projection sample of the projection sample (e.g., a neighboring projection sample prior to the projection sample or behind the projection sample), or the like, or any combination thereof. The determination of the modified sample information will be descried in detail in connection with FIG. 7.

Figure 7:
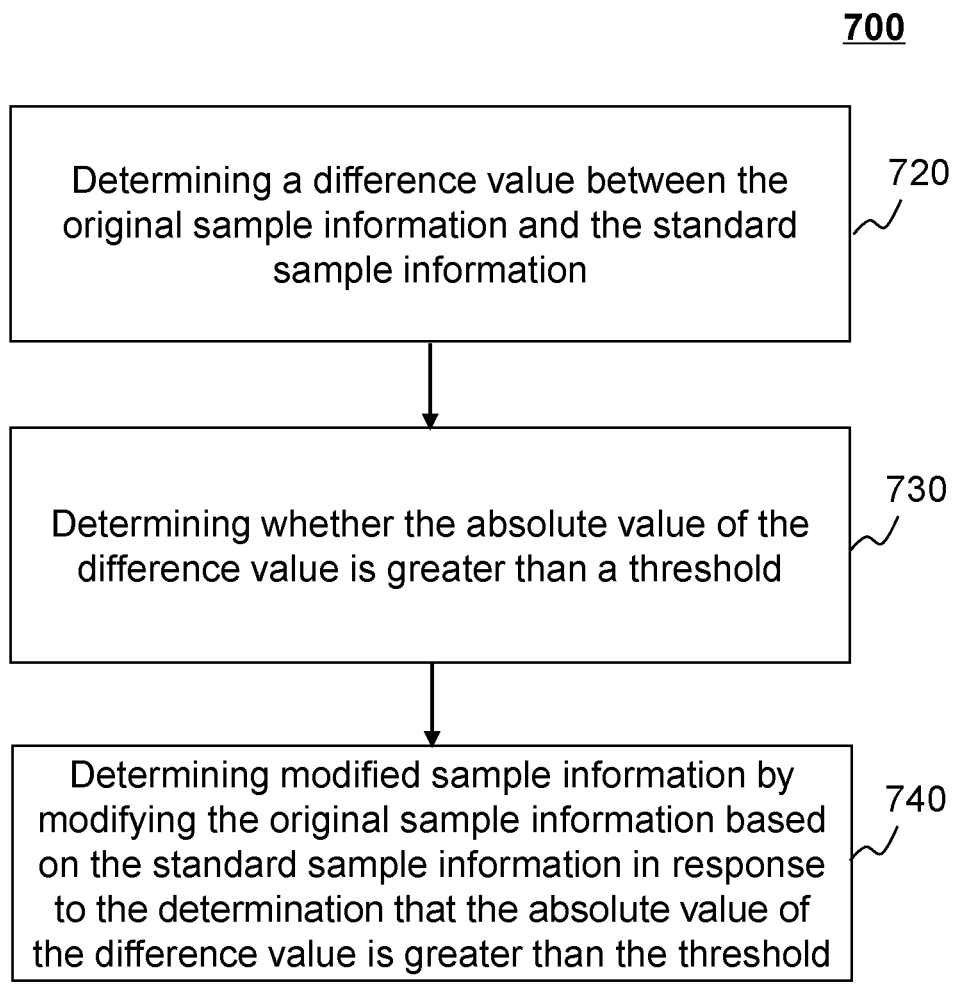
FIG. 7 is a flowchart illustrating an exemplary process for determining modified sample information according to some embodiments of the present disclosure.

FIG. 7 is a flowchart illustrating an exemplary process/method 700 for determining modified sample information according to some embodiments of the present disclosure. In some embodiments, the process/method 700 may be implemented in the system 100 illustrated in FIG. 1. For example, the process/method 700 may be stored in the database 150 and/or the storage device (e.g., the storage 220, the storage 390, the memory 360, etc.) as a form of instructions, and invoked and/or executed by the processing engine 140 (e.g., the processor 210 of the processing engine 140, or one or more modules in the processing engine 140 illustrated in FIG. 4) and/or the terminal 130 (e.g., the GUP 330 of the terminal 130, or the CUP 340 of the terminal 130). The operations of the illustrated process/method presented below are intended to be illustrative. In some embodiments, the process/method 700 may be accomplished with one or more additional operations not described, and/or without one or more of the operations discussed. Additionally, the order in which the operations of the process/method 700 as illustrated in FIG. 7 and described below is not intended to be limiting. In some embodiments, step 620 illustrated in FIG. 6 may be performed according to the process/method 700.

In 720, the modification module 430 may determine a difference value between the original sample information and the standard sample information. In some embodiments, the modification module 430 may determine a difference value between the original projection acquisition time and the standard projection acquisition time. In some embodiments, the modification module 430 may determine a difference value between the original rotation angle and the standard rotation angle. In some embodiments, the modification module 430 may determine a difference value between the original interval and the standard interval. In some embodiments, the modification module 430 may determine a difference value between the original angle difference and the standard angle difference.

In 730, the modification module 430 may determine whether the absolute value of the difference value is greater than a threshold. The threshold may be the default setting of the system 100.

In 740, the modification module 430 may determine modified sample information by modifying the original sample information based on the standard sample information in response to the determination that the absolute value of the difference value is greater than the threshold. For example, the standard projection acquisition time of the projection sample may be 30 milliseconds. The original projection acquisition time of the projection acquisition time may be 25 milliseconds. The absolute value of the difference value between the standard projection acquisition time and the original projection acquisition time may be 5 milliseconds that is greater than the threshold (e.g., 1 millisecond). The modification module 430 may determine the modified projection acquisition time as 30 milliseconds.

As another example, the standard interval may be 10 milliseconds. The original interval may be 5 milliseconds. The absolute value of the difference value between the standard interval and the original interval may be 5 milliseconds that is greater than the threshold (e.g., 1 millisecond). The modification module 430 may determine the modified interval as 10 milliseconds.

As still another example, the standard rotation angle of the projection sample may be 0.12 π. The original rotation angle of the projection sample may be 0.1 π. The absolute value of the difference value between the standard rotation angle and the original rotation angle may be 0.02 π (≈0.0628) that is greater than the threshold (e.g., 0.01). The modification module 430 may determine the modified rotation angle as 0.12 π.

As still another example, the standard angle difference may be 0.04 π. The original angle difference may be 0.02 π. The absolute value of the difference value between the standard angle difference and the original angle difference may be 0.02 π(≈0.0628) that is greater than the threshold (e.g., 0.01). The modification module 430 may determine the modified angle difference as 0.04 π.

In some embodiments, the modification module 430 may perform no modification on the original sample information in response to the determination that the absolute value of the difference value is less than or equal to the threshold.

Figure 8:
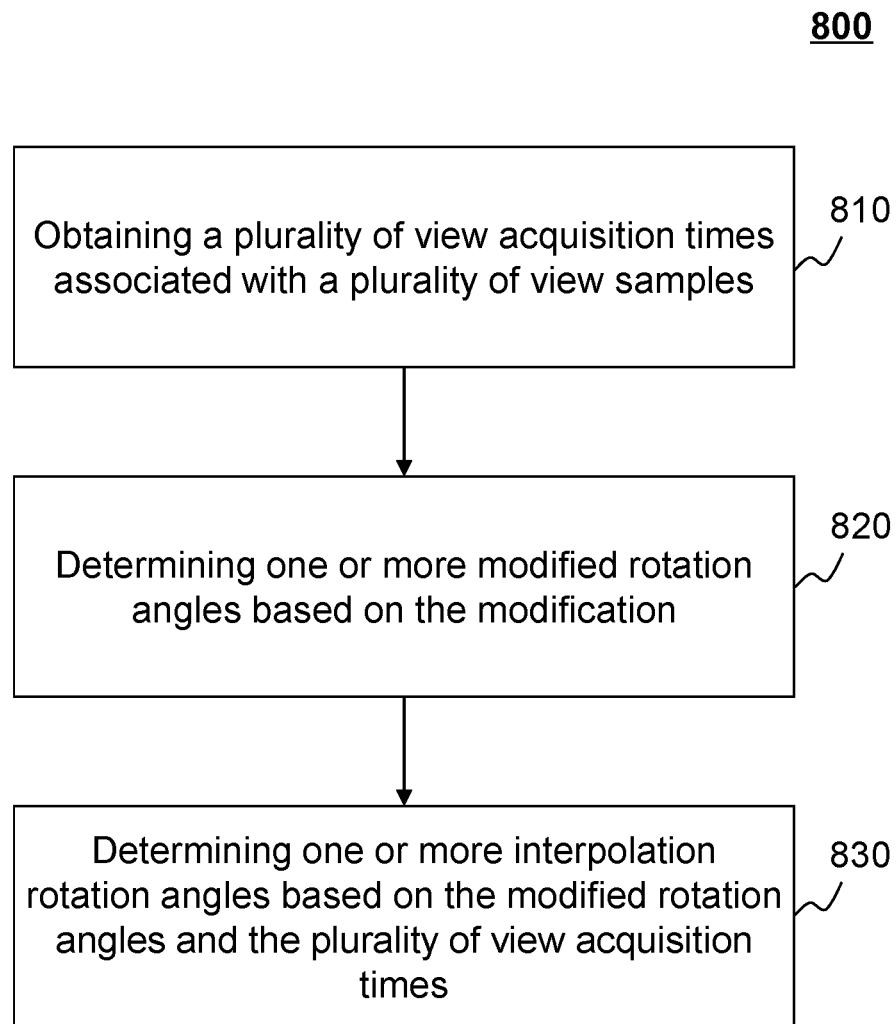
FIG. 8 is a flowchart illustrating an exemplary process for determining one or more new rotation angles according to some embodiments of the present disclosure.

FIG. 8 is a flowchart illustrating an exemplary process/method for determining one or more new rotation angles according to some embodiments in the present disclosure. In some embodiments, the process/method 800 may be implemented in the system 100 illustrated in FIG. 1. For example, the process/method 800 may be stored in the database 150 and/or the storage device (e.g., the storage 220, the storage 390, the memory 360, etc.) as a form of instructions, and invoked and/or executed by the processing engine 140 (e.g., the processor 210 of the processing engine 140, or one or more modules in the processing engine 140 illustrated in FIG. 4) and/or the terminal 130 (e.g., the GUP 330 of the terminal 130, or the CUP 340 of the terminal 130). The operations of the illustrated process/method presented below are intended to be illustrative. In some embodiments, the process/method 800 may be accomplished with one or more additional operations not described, and/or without one or more of the operations discussed. Additionally, the order in which the operations of the process/method 800 as illustrated in FIG. 8 and described below is not intended to be limiting. In some embodiments, step 540 illustrated in FIG. 5 may be performed according to the process/method 800.

In 810, the angle determination module 440 may obtain a plurality of view acquisition times associated with a plurality of view samples acquired during the CT scan. In some embodiments, in the CT scan, the detector 112 may perform a plurality of view samples to keep track of the attenuation of X-rays. In some embodiments, the CT scanner 110 may record a view acquisition time for a view sample. For example, the CT scanner 110 may add a time stamp to the view sample. The CT scanner 110 may store the plurality of view acquisition times in the database 150 and/or the storage device (e.g., the storage 220 of the processing engine 140, the storage 390 of the terminal 130, the memory 360 of the terminal 130, etc.). The angle determination module 440 may access the database 150 and/or the storage device to obtain the plurality of view acquisition times.

In 820, the angle determination module 440 may determine one or more modified rotation angles based on the modification.

In some embodiments, the modification module 430 may determine modified projection acquisition times by performing modification on the original projection acquisition times. The angle determination module 440 may determine the modified rotation angles based on the modified projection acquisition times. For example, the angle determination module 440 may determine a modified rotation angle of a projection sample by multiplying the modified projection acquisition time of the projection sample by the rotation speed of the radioactive scanning source 115.

In some embodiments, the modification module 430 may determine modified intervals by performing modification on the original intervals. The angle determination module 440 may determine the modified rotation angles based on the modified intervals. For example, the angle determination module 440 may determine a modified projection acquisition time based on the modified interval by determining the sum of the modified interval and intervals associated with projection samples prior to the projection sample, and determine a modified rotation angle by multiplying the modified projection acquisition time by the rotation speed of the radioactive scanning source 115. As another example, the angle determination module 440 may determine a modified angle difference by multiplying the modified interval by the rotation speed of the radioactive scanning source 115 and determine a modified rotation angle based on the modified angle difference.

In some embodiments, the modification module 430 may determine modified angle differences by performing modification on the original angle differences. The angle determination module 440 may determine the modified rotation angles based on the modified angle differences. For example, the angle determination module 440 may determine a modified rotation angle by determining the sum of the modified angle difference and angle differences associated with projection samples prior to the projection sample.

In 830, the angle determination module 440 may determine one or more new rotation angles based on the modified rotation angles and the plurality of view acquisition times. For example, in the CT scan, the CT scanner 110 may perform 4 view samples corresponding to 4 view acquisition times of $T_1$, $T_2$, $T_3$, and $T_4$, respectively, and the CT scanner 110 may perform 2 projections samples corresponding to 2 projection acquisition times of $T_1$ and $T_4$, respectively. The angle determination module 440 may determine 2 new rotation angles corresponding to $T_2$ and $T_3$, respectively. The angle determination module 440 may determine the one or more new rotation angles through a linear interpolation algorithm. For example, the angle determination module 440 may determine a new rotation angle between two rotation angles of two projection samples that are acquired in a same rotation of the radioactive scanning source 115 based on Formula (1) below:

$$\text{Angle}(x)=\text{alfa}*\text{Angle1}+(1-\text{alfa})*\text{Angle2} \quad (1)$$

wherein Angle (x) represents the new rotation angle; Angle 1 represents a rotation angle corresponding to a projection acquisition time prior to a new projection acquisition time corresponding to the new rotation angle; Angle 2 represents a rotation angle corresponding to a projection acquisition time behind the new projection acquisition time; and alfa may be expressed as Formula (2) below:

$$\text{alfa}=(\text{Time2}-\text{Time } x)/(\text{Time2}-\text{Time1}) \quad (2)$$

wherein Time x represents the new projection acquisition time corresponding to the new rotation angle; Time 1 represents the projection acquisition time corresponding to Angle 1; and Time 2 represents the projection acquisition time corresponding to Angle 2.

As another example, the angle determination module 440 may determine a new rotation angle between two rotation angles of two projection samples that are acquired in two neighboring rotations of the radioactive scanning source 115 based on Formula (3):

$$\text{Angle}(x)=\text{alfa}*\text{Angle1}+(1-\text{alfa})*(2\pi+\text{Angle2}) \quad (3)$$

In some embodiments, if the result of the new rotation angle is greater than $2\pi$, the angle determining module 430 may modify the new rotation angle by subtracting $2\pi$ from the new rotation angle.

It should be noted that the above description of the processing module is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, 820 may be omitted in the condition that the modification module 430 performs modification on the original rotation angle.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising:
   one or more storage media comprising a set of instructions for analyzing data from a computer tomography (CT) scanner; and
   one or more processors configured to communicate with the one or more storage media, wherein when executing the set of instructions, the one or more processors are directed to cause the system to perform operations including:
   obtaining a rotation speed of a radioactive scanning source in the CT scanner;
   obtaining a plurality of original projection acquisition times corresponding to a plurality of projection samples, the plurality of projection samples being associated with rotation of the radioactive scanning source; and
   determining, based on the rotation speed, a plurality of modified rotation angles corresponding to the plurality of projection samples by modifying a plurality of original rotation angles related to the plurality of original projection acquisition times.

2. The system of claim 1, wherein when executing the set of instructions, the one or more processors are directed to cause the system to perform operations including:
   generating, based on the plurality of modified rotation angles, one or more images.

3. The system of claim 2, wherein generating, based on the plurality of modified rotation angles, the one or more images includes:
   determining one or more interpolation rotation angles based on the plurality of modified rotation angles; and
   generating, based on the one or more interpolation rotation angles and the plurality of modified rotation angles, the one or more images.

4. The system of claim 3, wherein determining the one or more interpolation rotation angles based on the plurality of modified rotation angles includes:
   obtaining one or more view acquisition times associated with one or more view samples, the one or more view samples being associated with X-rays of the CT scanner; and
   determining the one or more interpolation rotation angles based on the one or more view acquisition times and the plurality of modified rotation angles.

5. The system of claim 1, wherein determining, based on the rotation speed, the plurality of modified rotation angles corresponding to the plurality of projection samples by modifying the plurality of original rotation angles related to the plurality of original projection acquisition times includes:
   determining the plurality of original rotation angles corresponding to the plurality of projection samples based on the plurality of original projection acquisition times and the rotation speed of the radioactive scanning source; and
   determining the plurality of modified rotation angles corresponding to the plurality of projection samples by modifying, based on standard information of the plurality of projection samples, the plurality of original rotation angles.

6. The system of claim 5, wherein determining the plurality of modified rotation angles corresponding to the plurality of projection samples by modifying, based on the standard information of the plurality of projection samples, the plurality of original rotation angles includes:
   obtaining a plurality of standard rotation angles corresponding to the plurality of projection samples, the standard information including the plurality of standard rotation angles corresponding to the plurality of projection samples;
   comparing the plurality of original rotation angles with the plurality of corresponding standard rotation angles, respectively; and
   modifying the plurality of original rotation angles based on the plurality of standard rotation angles and the comparison.

7. The system of claim 6, wherein obtaining the plurality of standard rotation angles corresponding to the plurality of projection samples includes:
  obtaining a sample number of the plurality of projection samples;
  determining, based on the sample number of the plurality of projection samples, a standard angle difference corresponding to any two neighboring projection samples arranged in time order; and
  determining the plurality of standard rotation angles based on the standard angle difference.

8. The system of claim 6, wherein obtaining the plurality of standard rotation angles corresponding to the plurality of projection samples includes:
  obtaining a sample number of the plurality of projection samples;
  determining, based on the sample number of the plurality of projection samples and the rotation speed of the radioactive scanning source, a standard time difference corresponding to any two neighboring projection samples arranged in time order;
  determining a standard angle difference corresponding to any two neighboring projection samples arranged in time order based on the rotation speed of the radioactive scanning source and the standard time difference; and
  determining the plurality of standard rotation angles based on the standard angle difference.

9. The system of claim 5, wherein determining the plurality of modified rotation angles corresponding to the plurality of projection samples by modifying, based on the standard information of the plurality of projection samples, the plurality of original rotation angles includes:
  obtaining a standard angle difference value corresponding to any two neighboring projection samples of the plurality of projection samples arranged in time order, the standard information including the standard angle difference value;
  determining a plurality of original difference values each of which corresponds to two neighboring original rotation angles of the plurality of original rotation angles arranging in order of time;
  comparing the plurality of the original difference values with the standard difference value, respectively;
  modifying the plurality of original difference values based on the standard difference value and the comparison; and
  determining the plurality of modified rotation angles based on the plurality of modified difference values.

10. The system of claim 1, wherein determining, based on the rotation speed, the plurality of modified rotation angles corresponding to the plurality of projection samples by modifying the plurality of original rotation angles related to the plurality of original projection acquisition times includes:
  determining a plurality of modified projection acquisition times corresponding to the plurality of projection samples by modifying, based on standard information of the plurality of projection samples, the plurality of original projection acquisition times; and
  determining the plurality of modified rotation angles corresponding to the plurality of projection samples based on the rotation speed of the radioactive scanning source and the plurality of modified projection acquisition times.

11. The system of claim 10, wherein determining the plurality of modified projection acquisition times corresponding to the plurality of projection samples by modifying, based on the standard information of the plurality of projection samples, the plurality of original projection acquisition times includes:
  obtaining a plurality of standard projection acquisition times corresponding to the plurality of projection samples, the standard information including the plurality of standard projection acquisition times corresponding to the plurality of projection samples;
  comparing the plurality of original projection acquisition times with the plurality of corresponding standard projection acquisition times, respectively; and
  modifying the plurality of original projection acquisition times based on the plurality of standard projection acquisition times and the comparison.

12. The system of claim 11, wherein obtaining the plurality of standard projection acquisition times corresponding to the plurality of projection samples includes:
  obtaining a sample number of the plurality of projection samples;
  determining a standard time difference value corresponding to any two neighboring projection samples of the plurality of projection samples arranged in time order based on the sample number of the plurality of projection samples and the rotation speed of the radioactive scanning source; and
  determining the plurality of standard projection acquisition times based on the standard time difference value.

13. The system of claim 10, wherein determining the plurality of modified projection acquisition times corresponding to the plurality of projection samples by modifying, based on the standard information of the plurality of projection samples, the plurality of original projection acquisition times includes:
  obtaining a standard time difference value corresponding to any two neighboring projection samples of the plurality of projection samples arranged in time order, the standard information including the standard time difference value;
  determining a plurality of original time difference values each of which corresponds to two neighbor original projection acquisition times of the plurality of original projection acquisition times;
  comparing the plurality of original time difference values with the standard time difference value, respectively;
  modifying the plurality of original time difference values based on the standard time difference value and the comparison; and
  determining the plurality of modified projection acquisition times based on the plurality of modified time difference values.

14. A method implemented on a computing device having one or more processors and one or more storage devices, the method comprising:
  obtaining a rotation speed of a radioactive scanning source in the CT scanner;
  obtaining a plurality of original projection acquisition times corresponding to a plurality of projection samples, the plurality of projection samples being associated with rotation of the radioactive scanning source; and
  determining, based on the rotation speed, a plurality of modified rotation angles corresponding to the plurality of projection samples by modifying a plurality of original rotation angles related to the plurality of original projection acquisition times.

15. The method of claim 14, wherein determining, based on the rotation speed, the plurality of modified rotation angles corresponding to the plurality of projection samples by modifying the plurality of original rotation angles related to the plurality of original projection acquisition times includes:
   determining the plurality of original rotation angles corresponding to the plurality of projection samples based on the plurality of original projection acquisition times and the rotation speed of the radioactive scanning source; and
   determining the plurality of modified rotation angles corresponding to the plurality of projection samples by modifying, based on standard information of the plurality of projection samples, the plurality of original rotation angles.

16. The method of claim 15, wherein determining the plurality of modified rotation angles corresponding to the plurality of projection samples by modifying, based on the standard information of the plurality of projection samples, the plurality of original rotation angles includes:
   obtaining a plurality of standard rotation angles corresponding to the plurality of projection samples, the standard information including the plurality of standard rotation angles corresponding to the plurality of projection samples;
   comparing the plurality of original rotation angles with the plurality of corresponding standard rotation angles, respectively; and
   modifying the plurality of original rotation angles based on the plurality of standard rotation angles and the comparison.

17. The method of claim 15, wherein determining the plurality of modified rotation angles corresponding to the plurality of projection samples by modifying, based on the standard information of the plurality of projection samples, the plurality of original rotation angles includes:
   obtaining a standard angle difference value corresponding to any two neighboring projection samples of the plurality of projection samples arranged in time order, the standard information including the standard angle difference value;
   determining a plurality of original difference values each of which corresponds to two neighboring original rotation angles of the plurality of original rotation angles arranging in order of time;
   comparing the plurality of the original difference values with the standard difference value, respectively;
   modifying the plurality of original difference values based on the standard difference value and the comparison; and
   determining the plurality of modified rotation angles based on the plurality of modified difference values.

18. The method of claim 14, wherein determining, based on the rotation speed, the plurality of modified rotation angles corresponding to the plurality of projection samples by modifying the plurality of original rotation angles related to the plurality of original projection acquisition times includes:
   determining a plurality of modified projection acquisition times corresponding to the plurality of projection samples by modifying, based on standard information of the plurality of projection samples, the plurality of original projection acquisition times; and
   determining the plurality of modified rotation angles corresponding to the plurality of projection samples based on the rotation speed of the radioactive scanning source and the plurality of modified projection acquisition times.

19. The method of claim 18, wherein determining the plurality of modified projection acquisition times corresponding to the plurality of projection samples by modifying, based on the standard information of the plurality of projection samples, the plurality of original projection acquisition times includes:
   obtaining a plurality of standard projection acquisition times corresponding to the plurality of projection samples, the standard information including the plurality of standard projection acquisition times corresponding to the plurality of projection samples;
   comparing the plurality of original projection acquisition times with the plurality of corresponding standard projection acquisition times, respectively; and
   modifying the plurality of original projection acquisition times based on the plurality of standard projection acquisition times and the comparison.

20. The method of claim 18, wherein determining the plurality of modified projection acquisition times corresponding to the plurality of projection samples by modifying, based on the standard information of the plurality of projection samples, the plurality of original projection acquisition times includes:
   obtaining a standard time difference value corresponding to any two neighboring projection samples of the plurality of projection samples arranged in time order, the standard information including the standard time difference value;
   determining a plurality of original time difference values each of which corresponds to two neighbor original projection acquisition times of the plurality of original projection acquisition times;
   comparing the plurality of original time difference values with the standard time difference value, respectively;
   modifying the plurality of original time difference values based on the standard time difference value and the comparison; and
   determining the plurality of modified projection acquisition times based on the plurality of modified time difference values.

* * * * *